United States Patent [19]

Humphrey

[11] Patent Number: 5,276,539
[45] Date of Patent: Jan. 4, 1994

[54] METHOD AND APPARATUS FOR CONTROLLING PERCEIVED BRIGHTNESS USING A TIME VARYING SHUTTER

[75] Inventor: John M. Humphrey, Monte Sereno, Calif.

[73] Assignee: Humphrey Engineering, Inc., Monte Sereno, Calif.

[21] Appl. No.: 908,829

[22] Filed: Jul. 2, 1992

Related U.S. Application Data

[62] Division of Ser. No. 628,323, Dec. 14, 1990, abandoned.

[51] Int. Cl.$^5$ .......................... G02F 1/133; G02C 7/10
[52] U.S. Cl. .......................................... 359/40; 359/85; 351/44; 351/158; 351/246
[58] Field of Search .................... 351/246, 201, 41, 44, 351/45, 158; 358/88, 92; 359/36, 38–

[56] References Cited

U.S. PATENT DOCUMENTS

| | | | |
|---|---|---|---|
| 3,603,305 | 9/1971 | Oppenheimer | 351/44 |
| 3,986,022 | 10/1976 | Hyatt | 250/205 |
| 4,021,846 | 5/1977 | Roese | 358/92 |
| 4,106,217 | 8/1978 | Witt | 359/94 |
| 4,279,474 | 7/1981 | Belgorod | 351/41 |
| 4,462,661 | 7/1984 | Witt | 359/40 |
| 4,688,895 | 8/1987 | Jacob | 359/85 |
| 4,698,668 | 10/1987 | Milgram | 358/92 |
| 4,792,850 | 12/1988 | Liptoh et al. | 358/92 |
| 4,842,400 | 6/1989 | Klein | 351/41 |
| 4,848,890 | 7/1989 | Horn | 351/44 |
| 4,968,127 | 11/1990 | Russell | 351/44 |
| 4,979,033 | 12/1990 | Stephens | 358/92 |
| 5,015,086 | 5/1991 | Okaue et al. | 351/44 |
| 5,067,795 | 11/1991 | Senatore | 351/41 |
| 5,113,270 | 5/1992 | Fergason | 359/37 |

*Primary Examiner*—William L. Sikes
*Assistant Examiner*—Tai V. Duong
*Attorney, Agent, or Firm*—John J. Leavitt; William A. Blake

[57] ABSTRACT

A method and apparatus is presented for successively interrupting the transmission of light through a transparent body at a frequency such that a scene viewed through the transparent body by a human eye is perceived as a continuous image that is less bright than actually, and is viewed with minimal color distortion. In one aspect of the invention, the lenses of spectacles are provided with a layer of liquid crystal material that is normally transparent, but which responds to the application of an electrical charge to render the liquid crystal layer non-transparent. By adjusting the frequency of application of successive electrical charges, the lenses admit light at full brightness for small increments of time, with minimal color distortion, and interrupt the transmission of light for small increments of time, so that the light admitted at full brightness is perceived as being less bright or dimmed. In another aspect, the transparent body is "nodalized" so that small increments of the body are independently responsive to successive electrical charges, whereby the brightness of light passing through such "nodes" is perceived as being less bright or dimmed.

16 Claims, 5 Drawing Sheets $I = I_o 2^{M-M_o}$, $I$ = LIGHT INTENSITY, $M$ = LIGHT METER READING

| OPEN AREA FRACTION | UNDIMMED LEFT BULB MEASURED THROUGH SHUTTER | | | RIGHT BULB DIMMED TO MATCH PERCEIVED LEFT BULB INTENSITY | | |
|---|---|---|---|---|---|---|
| | $M$ | $M-M_o$ | $I$ | $M$ | $M-M_o$ | $I$ |
| *BLACK BACKGROUND* | | | | | | |
| 1.0 | 5.5 | 0 | 1.0 | 5.8 | 0 | 1.0 |
| 0.38 | 3.9 | -1.6 | 0.33 | 5.0 | -0.8 | 0.57 |
| 0.25 | 3.3 | -2.2 | 0.22 | 3.8 | -2.0 | 0.25 |
| 0.13 | 2.3 | -3.2 | 0.11 | 2.6 | -3.2 | 0.11 |
| *GREEN BACKGROUND* | | | | | | |
| 1.0 | 5.7 | 0 | 1.0 | 6.0 | 0 | 1.0 |
| 0.38 | 4.1 | -1.6 | 0.33 | 5.1 | -0.9 | 0.54 |
| 0.25 | 3.6 | -2.1 | 0.23 | 4.0 | -2.0 | 0.23 |
| 0.13 | 2.5 | -3.2 | 0.11 | 3.0 | -3.0 | 0.13 |

FIG. 13

METHOD AND APPARATUS FOR CONTROLLING PERCEIVED BRIGHTNESS USING A TIME VARYING SHUTTER

This is a divisional of copending application Ser. No. 07/628,323 filed on Dec. 14, 1990, now abandoned.

BACKGROUND OF THE INVENTION

1. Field of the Invention

This invention relates to the control of brightness perceived by the human eye, and more particularly to a method and apparatus that achieves such control using a nodalized time-varying shutter (NTVS).

2. Description of the Prior Art

A premilinary patentability and novelty search conducted in connection with the invention or inventions disclosed herein has revealed the existence of the following United States Patents:

| | | |
|---|---|---|
| 3,245,315 | 3,409,909 | 3,441,513 |
| 3,575,491 | 3,576,761 | 3,585,381 |
| 3,591,810 | 3,603,305 | 3,630,603 |
| 3,617,374 | 3,620,889 | 3,661,142 |
| 3,692,388 | 3,704,625 | 3,720,623 |
| 3,893,340 | 4,087,575 | 4,180,722 |
| 4,261,651 | 4,272,164 | 4,278,349 |
| | 4,393,400 | |

Of the patents listed above, five appear to be more pertinent than the others. These are identified as U.S. Pat. Nos. 3,245,315; 3,409,909; 3,603,305; 3,630,603 and 4,272,164.

Referring to these patents in the order in which they issued, it is noted that U.S. Pat. No. 3,245,315 discloses a light controlling device that is particularly adapted to protect the eyes from flashblindness. A sensor mounted on the spectacle frame "sees" the flash and initiates the application of an electric charge on the electro-optic crystal material included in the lenses, resulting in the lenses becoming opaque for the duration of the flash and then reverting to transparency. Also disclosed by this patent is a method for controlling brightness by reducing the steady-state light intensity reaching the eyes of the wearer of the spectacles through adsorption of the light impinging on the lenses. This mode of operation is fundamentally different from the mode disclosed and claimed herein wherein the brightness of a source of light is not diminished per se, but the perception of brightness is controlled by reducing the time that the light impinges on the eyes.

U.S. Pat. No. 3,409,909 discloses a device to protect against flashblindness of the type that might be imposed by the explosion of an atomic bomb. A light sensor initiates the release and dispersion of an opaque liquid on the interior of a cavity between two transparent lenses, thus attenuating the light seeking to pass through the lenses.

U.S. Pat. No. 3,603,305 does not relate to brightness control. Rather, this patent is directed to a sensory development apparatus, conveniently in the form of spectacles, useful to aid in the "fusion" process that occurs in the brain of a human to perceive the images transmitted to the retina of the eyes. Stated in other words, the apparatus described by this patent is particularly useful to aid visually impaired individuals to achieve visual fusion.

U.S. Pat. No. 3,630,603 describes spectacles incorporating lenses that can be darkened to reduce the steady-state light level reaching the eyes. Brightness control is achieved through steady-state dimming as with conventional sunglasses.

U.S. Pat. No. 4,272,164 describes a device to protect image intensifiers from glare using an electochemical material.

Thus, it will be seen that the devices discussed above all reduce the steady state light level by turning partially or totally opaque with the level of brightness controlled by the degree of opacity as in conventional sunglasses. This is clearly different from the invention disclosed herein which controls perceived brightness by controlling the fraction of time during which ambient light, ideally with minimum alteration, enters the eye.

Everything that a human sees is light-packets of energy called "quanta" that move in waves as a small part of the band of electromagnetic radiation that reaches Earth from the stars and galaxies, or from some artificial source of such light. The human eye is so sensitive to light that it has been stated that as few as ten quanta, roughly equivalent to the glow of a candle at a distance of ten miles, will stimulate the human eye. The Mammalian eye has evolved to function over a wide range of ambient light levels. Since the retina has a limited capacity to handle different levels of light intensity, nature has provided other structures to expand this range. Thus, the iris provides the primary mechanism for controlling the amount of light entering the eye. The eyebrows together with the squinting reflex both shade the eye from direct sunlight and help provide another means of coping with excessively bright light conditions. Mankind has heretofore assisted nature by inventing conventional sunglasses which reduce the amount of steady-state light reaching the retina by filtering the light with semi-transparent glass or plastic material. All these structures: the iris, squinting and conventional sunglasses allow the eye to function in brighter light by reducing the steady-state light intensity reaching the retina.

Accordingly, one of the important objects of the present invention is the provision of a method and apparatus for controlling the perceived brightness of light from a source thereof when viewed by a human eye.

Another object of the invention is the provision of a method and apparatus for controlling the perceived brightness of light from a source thereof by controlling the time of exposure of the eyes to the light.

Still another object of the invention is the provision of a method and apparatus for controlling the perceived brightness of light from a source thereof by periodically interrupting the light to which the eyes are simultaneously exposed at a frequency that is undetectable by the human eye.

Yet another object of the invention is the provision of a method and apparatus, including a pair of spectacles having lenses therein, operative to control the time interval during which light passes through the lenses to control the perception of brightness of the light impinging on the eye.

A still further object of the invention is the provision of a method and apparatus, including a pair of spectacles having lenses therein for the simultaneous admission of light to both eyes, wherein both lenses include a layer of liquid crystal material the transparency of which may be controlled by the application of an electric voltage.

Yet another object of the invention is the provision of a method and apparatus for controlling the perceived brightness of a source of light viewed by human eyes, including a pair of spectacles having lenses incorporating liquid crystal material the transparency of which may be selectively controlled by the application of an electric voltage, the area of the lenses being "nodalized" to define areas of the lenses that automatically react independently of other areas thereof to reduce the perceived brightness of light passing through a given "node."

One of the problems that has vexed the sunglass industry has been the inability to provide sunglasses for human wear that did not alter the perception of color by the wearer. Accordingly, another object of the present invention is the provision of a pair of spectacles including lenses equipped with means for controlling the brightness of the light impinging on the human eye while minimally distorting the color content of the light perceived.

A still further object of the invention is the provision of a method of interdependently controlling multiple nodes of a "nodalized" transparent body to control both brightness and contrast between "nodalized" areas of the transparent body.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the method and apparatus of the invention in one aspect is operative to intercept the transmission of light to the eyes of a human at a frequency undetectable by the human eye, thereby to control the perceived brightness of the light. In terms of structure, this result is accomplished by providing a pair of spectacles equipped with a time-varying shutter (TVS) operative by the controlled application of an electric voltage to modulate the ON/OFF time that light is permitted to pass through the time-varying shutter. In a second aspect of the invention, the time-varying shutter is "nodalized" by arranging distinct and separate areas or "nodes" of the time-varying shutter that automatically react to the imposition of light thereon to effect control of the brightness of the light passing through that particular area or node. Structurally, this is accomplished by sensing the "quanta" of light impinging on a given node, and applying an electrical voltage to the node material to effect modulation of the light passing through that node to thus reduce the brightness of light passing therethrough. To accomplish this purpose, a pair of spectacles are provided with lenses that include a "nodalized" layer of liquid crystal material that reacts node by node to the imposition of an electric voltage by becoming opaque to the transmission of light therethrough.

When the voltage is removed, the liquid crystal material again becomes transparent to the passage of light. Means are provided in conjunction with such lenses to sense and "quantify" the "quanta" of light impinging on the lenses either over the entire area of the lenses, or over "nodalized" areas thereof. An electronic control means is provided to receive a signal from the light sensor means and controls the fraction of time during each voltage cycle that voltage is applied to the liquid crystal film to thus render it opaque. For a "nodalized" application, a single oscillator circuit drives many "dimming" circuits, each controlling the transparency of a particular "node" in response to the light level in that part of the field. One or more manual controls may be provided to override the automatic controls. The system is powered by an appropriate battery, the charge of which may be maintained by a solar cell assembly built into or secured to the spectacle structure.

BRIEF DESCRIPTION OF THE DRAWINGS

FIG. 13 is a tabulation of the results of the experiments conducted with the apparatus of FIG. 9 utilizing the three disks of FIGS. 10, 11, and 12.

DESCRIPTION OF THE PREFERRED EMBODIMENT

Figure 3:
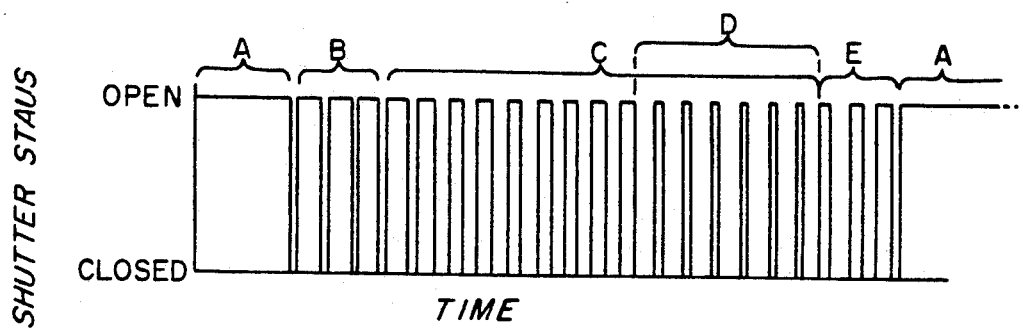
FIG. 3 is a graph correlated to the graph illustrated in FIG. 2, but plotting shutter status as the ordinate against time as the abscissa for a spectacle lens constituting a single node time varying shutter.

In terms of greater detail, the time varying shutter apparatus of my invention is illustrated and described as embodied in a pair of spectacles operable to create the perception of reduced brightness of a source of light even though the actual brightness of the light is undiminished. This perception is created by fully interrupting the transmission of light to both eyes of the observer in sequential time intervals of sufficient frequency that the observer is unaware of the interruption and sees the light as a continuously illuminated source of light having decreased brightness correlated to the time of exposure of the eyes to the light. In other words, once a frequency of oscillation sufficiently high to eliminate flicker has been selected and implemented, that frequency may be maintained constant while the time interval in each cycle that light is fully interrupted determines the length of time that the eye is exposed to the light. Thus, the dimming ratio is determined by the correlating of ON time to OFF time in each cycle, the OFF time representing a lens open (transmissibility) condition, while the ON time represents a lens closed (non-transmissibility) condition. This mode of operation is illustrated in FIG. 3 of the drawings.

It is a matter of common knowledge that conventional sunglasses do not completely eliminate the transmission of light to the eyes through the lenses. Rather, conventional sunglasses function to absorb a certain amount of the light, or to absorb light rays within a specific band of frequencies while reflecting light rays of other unwanted or harmful frequencies. It is also well know that such "steady-state" absorption of light by conventional sunglasses has a drastic affect on the perception of color as seen through such sunglasses.

It is my contention that time varying shutter (TVS) sunglasses, i.e., sunglasses that control the fraction of time light enters the eye, will be perceived by the observer as a reduction in the brightness of the light. It is also my contention that the use of my time varying shutter apparatus and method results in the perception of reduced brightness with a minimum of color distortion.

Figure 9:
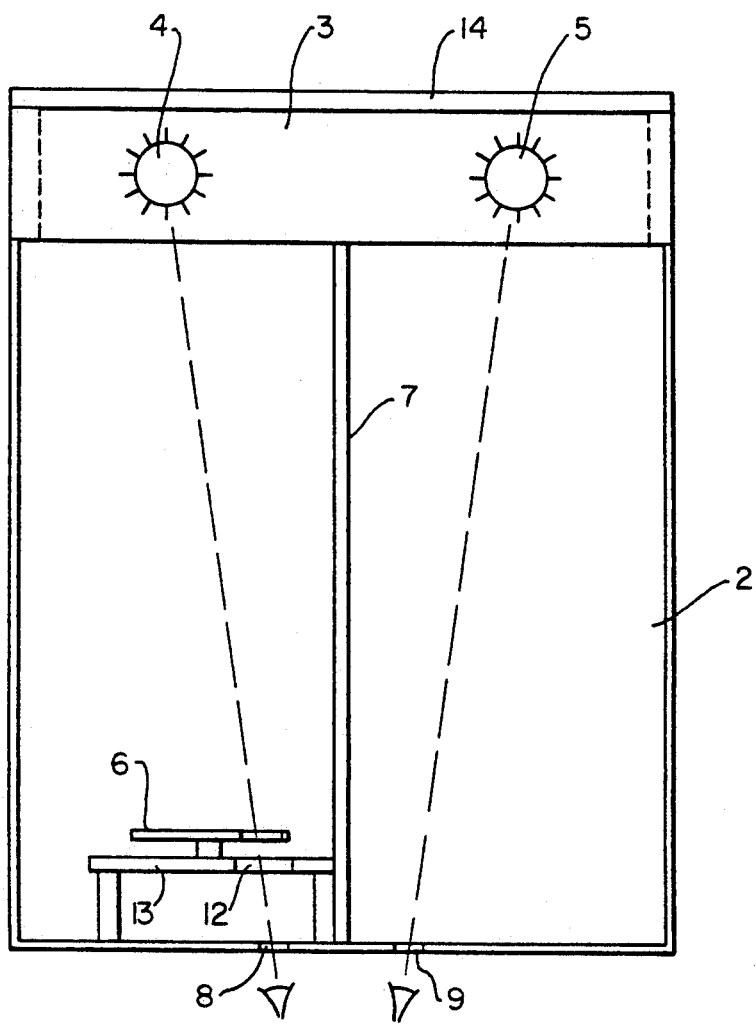
FIG. 9 is a plan view of an experimental device utilized to prove the theory that decrease of the time of exposure of the eye to a uniformly bright object results in the perception of the object as being less bright than actually.

It is surprising that given the level of liquid crystal technology as evidenced by the United States patents listed above, that no one has heretofore discovered what I have discovered, that by rapidly totally interrupting the transmission of light to the eyes of an observer, the observer perceives the light as being of less brightness than is actually the case. To prove this novel theory, experiments were conducted utilizing the very rudimentary apparatus illustrated in FIG. 9. The apparatus comprises merely a base structure 2 on which is mounted a pedestal 3, on which pedestal are mounted two electric light bulbs 4 and 5, each connected to a source of alternating current power (not shown) to illuminate the bulbs, with the bulb 5 on the right being connected to a suitable dimming reostat (not shown) actuable to selectively reduce the power to the right hand bulb to thus effect dimming of this bulb.

The two bulbs are mounted on one end of the base member, while on the other end of the base there is rotatably mounted an apertured disk 6 suitably connected to a motor (not shown) that will rotate the disk at least at a constant twenty-two times per second, this being an approximate minimum frequency of interruption of the light at which the light interruption will not be perceived by the observer, and the light will appear to be continuously illuminated. Also mounted on the base is a vertical partition 7 arranged so that the left eye 8 of an observer views the light bulb 4 through the aperture formed in the disk, while the right hand bulb 5 is viewed by the right eye 9 of the observer without interruption of the transmission of light therefrom. The construction of the panel 7 is such that the right eye cannot see the left hand bulb, and the left eye cannot see the right hand bulb. The observer is provided access to the dimming switch, which may be manipulated to effect dimming of the right hand bulb to a perceived brightness equal to the brightness of the left hand bulb as seen by the left eye through the rapidly rotating aperture in the disk and the port 12 in the panel 13 when the aperture in the disk and the port 12 are in registry.

Figure 10:
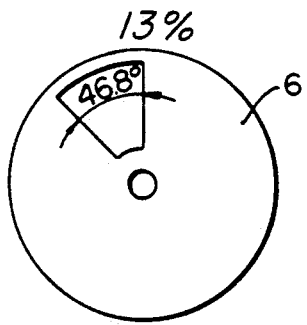
FIG. 10 is a front elevational view of a rotatable disk mounted in the device of FIG. 9 in a manner to enable sequential interruption of the transmission of light to the left eye of an observer from an illuminated electric light bulb at a rate such that the light bulb is perceived by the observer as being continuously illuminated but at decreased brightness correlated to the time interval that the left eye is exposed to the light, while the right eye is continuously exposed to the light from a similar electric light bulb. The disk illustrated possesses a port or opening for transmission of light from the left bulb, the port being only thirteen percent (13%) of the total area of the disk.
Figure 11:
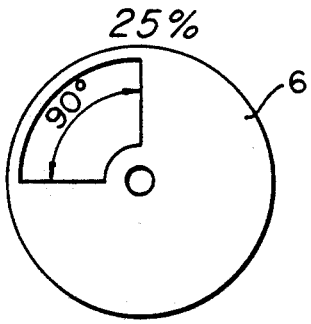
FIG. 11 is a view of a disk similar to the disk of FIG. 10 but having an opening that is twenty-five percent (25%) of the area of the disk.
Figure 12:
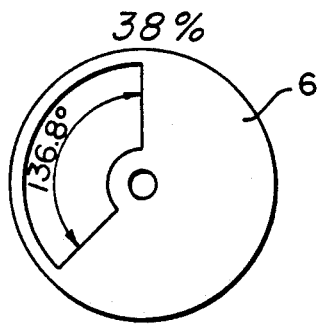
FIG. 12 is a view of a disk similar to the disk of FIG. 10 but having an opening that is thirty-eight percent (38%) of the area of the disk.

FIG. 10 illustrates a disk 6 in which the aperture in the disk encompasses approximately thirteen percent (13%) of the total area of the disk. In FIG. 11, the disk 6 was provided with an aperture that encompassed approximately twenty-five percent (25%) of the area of the disk, and in the disk illustrated in FIG. 12, the aperture encompassed approximately thirty-eight percent (38%) of the area of the disk. Each of the disks in turn were mounted in the apparatus and two test series were conducted. The first test series was conducted with a black background provided by the panel 14, and the second test series was conducted with a green panel substituted for the black panel, it being realized that there would be a difference in light reflectivity from the two different panels, and it was important to determine the effect on color perception during the tests.

The test series proceeded by having an observer view the illuminated left bulb with his left eye through the rapidly rotating disk while simultaneously viewing the illuminated right bulb with his right eye with no obstruction of the view. The observer then gradually causes dimming of the right bulb until the brightness of the right bulb as seen by the right eye matches the perceived brightness of the left bulb as seen by the left eye. After the brightness of the right bulb has been adjusted to match the perceived brightness of the left bulb, a light meter was used to measure the light intensity or brightness of both the dimmed right bulb and the left bulb as viewed by the light meter through the aperture of the spinning disk. The three different shutters illustrated in FIGS. 10, 11 and 12 were used sequentially in the test series to evaluate the effect of duty cycle on perceived brightness. Additionally, black and green colored backgrounds were used to evaluate color perception at reduced perceived light levels.

The data from these test is tabulated in FIG. 13. The light meter graduations were set so that each unit increase in meter reading represented a doubling of the light level. Consider first the data taken for the undimmed left bulb 4 through the "shutter" represented by the disk 6. The first reading was taken with the shutter disk stationary and the aperture in the disk positioned in registry with the port 12 so that light from the undimmed left bulb entered the light meter unimpeded. The other readings were taken with the shutter disk rotating several thousand revolutions per minute, sufficient to provide a variable "shutter" with at least twenty-two cycles per second. It will be seen from the tabulation of data in FIG. 13 that the light intensity readings from the light meter closely match the open area fractions of the total area of the disks. It will also be noted that the absolute readings for the green background are slightly higher due to the greater reflectivity of the green background.

During each test, the right bulb was dimmed until its brightness appeared to match the left bulb as viewed through the shutter. Although the color of the right bulb changed as it was dimmed, it was possible to match the total brightness of the two bulbs. The test results, as indicated in FIG. 13, verified the time varying shutter (TVS) technique postulated above for perceived brightness attenuation. It is clear from the data that as the area of the aperture in the disk decreased, the observer perceived a significant reduction in brightness of the left bulb even though its actual brightness had not been diminished. This perception of reduced brightness of the left bulb 4 is indicated clearly by the level of dimming required of the right bulb to match the perceived brightness of the left bulb viewed through the shutter disk.

The tests clearly demonstrate that large changes in perceived brightness of a source of light can be achieved through use of my time varying shutter technique. With the 13% aperture disk in place, it required dimming of the right bulb to almost extinguishment to match the perceived brightness of the left bulb seen through the rotating disk. With the 13% and 25% aperture disks in place, the perceived brightness as measured by the light meter after dimming, closely matched the aperture area/total disk area ratio. However, with the 38% aperture area disk in place, it was found that there was a significant difference in the correlation between the perceived brightness of the left bulb based on the measured light intensity of the dimmed right hand bulb and the actual brightness of the left hand bulb as measured by the light meter through the rapidly rotating disk aperture. It is not known whether this indicates some non-linearity in human brightness perception. If so, the time varying shutter duty cycle can be designed to handle this effect. However, the most important result shown by the tests, despite the rudimentary test apparatus, is that "shutter" duty cycles that will provide 13% to 25% "open" i.e., transparent lenses, are practical applications for liquid crystal display shutters, and that these duty cycles can achieve perceived brightness reductions of the same order, i.e., by a factor of from four (4) to eight (8), which is sufficient for most sunglasses applications. It is clear therefore that the 13% to 25% "open" condition, i.e., transparent lens condition, is correlated to the time interval that the remainder of the disk blocks the light from passing through the aperture. Thus, while maintaining a constant rotational speed, varying the percentage of the disk opaque to the transmission of light directly controls the fraction of time that the eye is exposed to the light from the light bulb.

The test results also verified the lack of color distortion with time varying shutter brightness reduction. Although the left bulb was perceived to be much dimmer viewed through the rotating shutter disk, the bulb maintained a clear white color. The green background was also perceived as a bright green even with the 13% aperture area disk. Since contrast in color is such an important part of visual perception, the ability to achieve dimming without color distortion is considered to be a major advantage of time varying shutter brightness reduction according to this invention.

Figure 1:
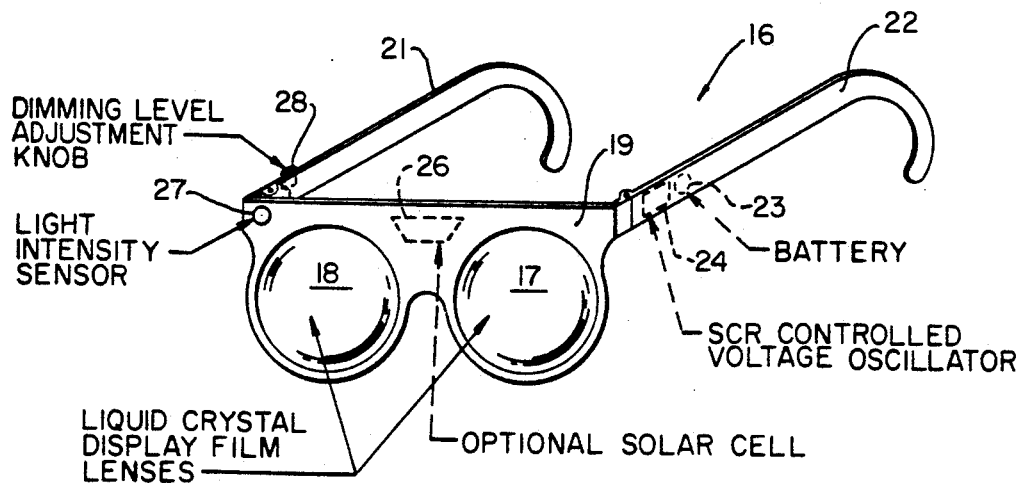
FIG. 1 is a perspective view of sunglass spectacles incorporating the liquid crystal method and means for controlling the transparency of the lenses.

My time varying shutter theory as discussed above, and as proven by the test results tabulated in FIG. 13, are applied to a practical structure in the form of spectacles designated generally by the numeral 16 in FIG. 1. As there shown, the spectacles include left and right eye lenses 17 and 18, each of which may constitute a single "node" lens incorporating liquid crystal material of the type that may be rendered opaque to the transmission of light by the application of an electric charge thereto, and rendered transparent to the transmission of light by the removal of such electric charge. In this aspect of the invention, the entire area of each of the lenses is normally simultaneously transparent. The entire area of each of the lenses is simultaneously rendered opaque by the simultaneous application to both of the lenses of an appropriate electrical charge. The electrical charge is applied at a frequency such that the eyes do not discern that there has been a complete interruption of the transmission of light thereto. Such a frequency is preferably twenty-two (22) cycles per second or greater.

In the interest of brevity in this description, particularly since the specific liquid crystal material utilized herein does not constitute the invention described and claimed herein, a specific liquid crystal material is not described herein, it being believed that such materials are readily identifiable from the prior art noted above through a process of selection. Rather, this invention is directed to the implementation of such available and appropriate liquid crystal materials in the formation of the lenses 17 and 18 of a spectacle-type device that includes a frame 19 to support the lenses 17 and 18 in position in front of the eyes of an observer, the frame being provided with temple members 21 and 22 in the usual fashion.

As illustrated in FIG. 1, there is mounted in the temple 22 an appropriate battery 23 to power the device, and provide requisite electrical voltage to a silicon controlled rectifier 24 also mounted in the temple 22 in association with the battery 23 and connected thereto. Optionally, there is provided a solar cell 26 mounted in the frame 19 as illustrated, the solar cell being operative to keep the battery 23 charged to an operative level. Also provided on the frame 19 is a light intensity sensor designated generally by the numeral 27 and included in the control circuit that connects the solar cell, silicon controlled rectifier and battery to control the amount of electrical power delivered to the liquid crystal material forming a part of lenses 17 and 18. For the greater convenience of the wearer of the spectacles, there is provided an adjustment knob 28 on the spectacle frame that may be manipulated by the wearer to adjust the level of brightness that is desired by the wearer under different conditions.

It will thus be seen that the spectacles illustrated in FIG. 1 that embody my time varying shutter effectively replace standard or conventional sunglasses. As stated above, conventional sunglasses control the exposure of the eyes to the ambient light by reducing the steady state light intensity reaching the eyes. By contrast, my time varying shutter spectacles control the amount of light reaching the eyes by reducing the duration of exposure in point of time rather than by reducing the steady state light intensity. Investigation has revealed that the human visual response has a cycle time of about 50 milliseconds. Therefore, images that change at least twenty times a second are perceived as continuous. This theory is utilized in movie cameras which operate at about 22 frames per second to achieve a visually perceived continuous image.

The spectacles or glasses illustrated in FIG. 1 have, an electronic control system 24 that generates a series of ON/OFF voltage pulses to the liquid crystal displays in each lens. These liquid crystal displays are energized simultaneously so that the condition of the lens 17 is exactly matched by the condition of the lens 18. The duration of the ON pulses which result in rendering the lenses opaque, is determined by the strength of the signal from the light level sensor 27, including the rate of brightness increase, compared to the desired level of brightness as will hereinafter be explained. The adjustment knob 28 may be manipulated by the wearer to selectively control the desired level of brightness.

Figure 2:
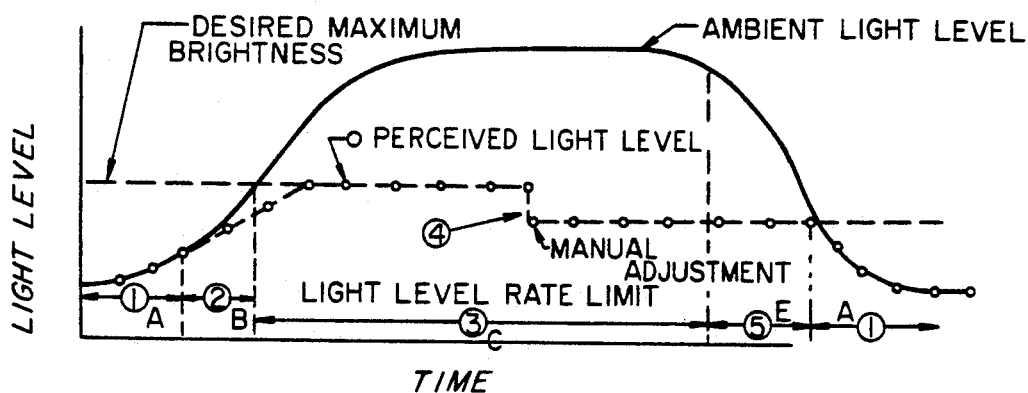
FIG. 2 is a graph illustrating the programmable capabilities of sunglasses equipped with lenses constituting single node time varying shutters according to the invention with light level being plotted as the ordinate value and time plotted as the abscissa value.

Operation of the time varying shutter (TVS) sunglasses during a hypothetical light level transient such as might occur while leaving a building in bright sunlight and then re-entering is shown in FIG. 2. As illustrated, initially, as shown in the graph, the light level within the building is below the desired brightness so the shutter does not operate, i.e., the shutter does not close, thus does not condition the lenses to reduce the time interval for which the eye is exposed to the light. As the light level increases, however, the brightness remains below the desired level but the rate of increase in brightness is too rapid for the eyes to comfortably accommodate. A built-in rate limit causes the shutter to operate at greater than 22 cycles per second to limit the rate of perceived brightness increase. As the brightness increases further, the TVS duty cycle increases the fraction of time the shutter is closed to maintain the perceived brightness at the desired maximum brightness level. At some point, the wearer decides to manually lower the desired maximum brightness level, and the duty cycle increases to reduce the perceived brightness to the new desired level. As the wearer re-enters the building, the light level rapidly decreases, but the shutter duty cycle follows the transient until the level falls below the desired brightness at which point the shutter remains open. By comparing the illustrations in FIGS. 2 and 3, it will be seen that the shutter status illustrated in FIG. 3 follows closely the transient light conditions illustrated in FIG. 2.

From the above, it is clear that TVS sunglasses offer several important advantages over conventional sunglasses. TVS sunglasses offer automatic adjustment for different light conditions. Most sunglasses have a fixed transmissibility. Darkly tinted glasses provide too much light reduction under moderately bright conditions, while lightly tinted glasses do not provide enough light reduction under bright conditions, such as snow or beach conditions. TVS sunglasses, on the other hand, adjust to the ambient light level to provide a consistent brightness to maximize perception and comfort.

Additionally, TVS sunglasses offer the capability for rapid response to varying light conditions as illustrated in FIGS. 2 and 3. Conventional sunglasses either have fixed light transmissibility or respond slowly to ambient light conditions. TVS sunglasses' response is limited only by the response capabilities of the liquid crystal display. This means that even for rapid light level transients, the user will perceive nearly a constant light level. Typical light level transients range from entering or leaving a building which requires a response time on the order of one second as illustrated in FIGS. 2 and 3, to playing sports, such as tennis, with rapid changes in orientation relative to the sun or to driving along a tree-lined street with rapidly alternating patches of sunlight and shade both of which require a response time of about 0.1 second. Both these times are long compared to the shutter cycle time and the LCD response time (a few milliseconds). Therefore, the TVS sunglasses provide the wearer with nearly constant perceived brightness during most activities where brightness reduction is desired.

It is sometimes necessary or desirable that the eyes be protected from sudden brightness as when emerging from a dark building. TVS sunglasses offer the capability of limiting the rate of increase of perceived brightness. Thus, the TVS sunglasses may be programmed to limit the rate of increase in perceived brightness (even when the absolute brightness is below the desired brightness) to aid this transition.

As stated above, conventional sunglasses distort the color of objects being viewed by the wearer. TVS sunglasses, on the other hand, offer the advantage of no color distortion of the object viewed. Such sensed brightness variations between nodes may be utilized, as in the example provided by the illustration in FIG. 6, to darken the sky and "illuminate" the airplane, i.e., provide contrast between the associated nodalized areas, so as to render the airplane more readily visible against the background of the sky. Since the amount of light reaching the eyes is limited by the exposure in point of time rather than the steady state transmissibility of the lenses, TVS sunglasses do not distort color like conventional tinted sunglasses. This enhances activities like sports which often require good color contrast and which are impaired by the color distortion of conventional sunglasses. The combination of optimal brightness without color distortion provides optimal contrast which should significantly enhance activities that rely on visual perception in bright light conditions. Because the eyes of every individual differ, TVS sunglasses offer easy adjustment for individual preferences. Some individuals prefer a brighter light level while others prefer one that is more subdued. Health conditions such as allergies or medicines (e.g. eyedrops) can also effect the light level that feels comfortable. The adjustment knob allows each individual to set the light intensity that feels comfortable for his particular needs.

Figure 4:
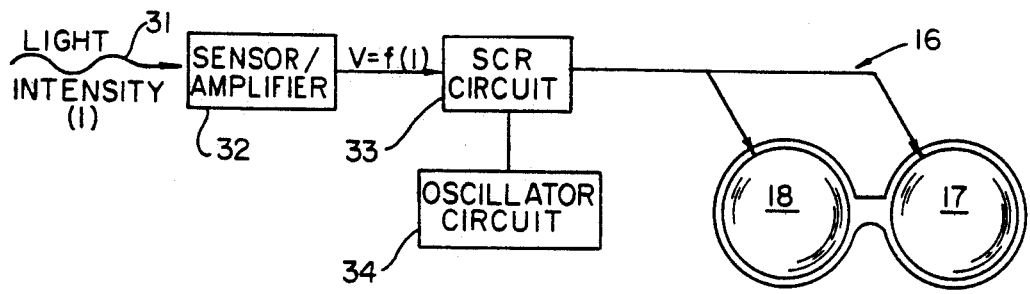
FIG. 4 is simplified diagram of the operating circuit of a single node time varying shutter system as applied to eye glasses.

The operation of the single node TVS sunglasses can be more easily be understood by referring to the block diagram shown in FIG. 4. This block diagram illustrates one very simple approach to implementing TVS brightness control. It is not intended by this illustration to restrict or limit the use of more elaborate circuits to control the duty cycle (i.e., the fraction of time that light is blocked by the liquid crystal film during each oscillator circuit half cycle) of the glasses.

Referring to FIG. 4, it will be seen that light of a specific intensity from a light source 31 impinges on a sensor/amplifier 32, the output voltage of which is a function of the light intensity. The output voltage from the sensor/amplifier 32 is applied to the silicon controlled rectifier (SCR) circuit 33, which also receives a square wave alternating current voltage from the oscillator circuit 34. The signal frequency from the oscillator is controlled to produce the frequency desired for TVS operation, generally 20 Hz or greater. The SCR circuit operation is analogous to the operation of a light dimming switch for controlling a conventional incandescent lamp. It uses the sensor/amplifier voltage to control the duration of each half square wave from the oscillator circuit that is transmitted to the liquid crystal film on the glasses. When the voltage is below a threshold value corresponding to the desired maximum brightness as indicated in FIG. 2, the SCR totally truncates the oscillator circuit signal so that the liquid crystal film is continuously deenergized, i.e., 100% open or transparent to the maximum extent possible considering the characteristics of the particular liquid crystal material being utilized.

This condition of operation is illustrated in FIGS. 2 and 3, where it is seen that the "open" shutter interval (A) corresponds to the rising curve (A) representing increasing brightness of the ambient light level. As the sensor/amplifier voltage increases during the interval (B) as a result of the increased rate of increase of brightness toward the desired maximum brightness, it will be seen that the "open" condition of the shutter is altered a number of times by complete closure thereof to control the perceived light level to a rate that increases at a slower rate than the rate of increase of the ambient light level. This results in the perceived light level corresponding to the desired maximum brightness level being reached later in time than the ambient light level reaches the threshold level at which the liquid crystal shutter is activated.

Thus, while the ambient light level continues to rise above the threshold level to a maximum during the interval (C), the SCR allows progressively more of the oscillator circuit signal to pass to the glasses to be applied to the liquid crystal film, thus maintaining the perceived light level constant until altered voluntarily by the wearer of the glasses at point (D), where the control knob 28 is manipulated to selectively lower the perceived light level to a more comfortable level, for instance. This more comfortable level of perceived brightness may be maintained through the intervals (D) and (E) despite the reduction in ambient light level that occurs in the interval (E) during which the ambient light level drops to coincide with the perceived brightness, at which point the oscillator circuit signal is again truncated to again "open" the lenses to achieve maximum transparency. The SCR circuit also contains a full wave rectifier so that the glasses receive a series of positive voltage pulses whose duration increases as the sensor/amplifier voltage increases as a function of the increasing intensity of the light from the light source. Consequently, as the sensor/amplifier voltage increases so does the "duty cycle" of the glasses, whereby the perceived brightness through the lenses is maintained at the desired level. It will of course be apparent that the sensor/amplifier can incorporate the ability to adjust the output voltage based on many different parameters, such as (a) non-linearities in human brightness perception; (b) the rate of change of light intensity, and (c) an adjustable threshold level at which the shutter is activated.

Figure 5:
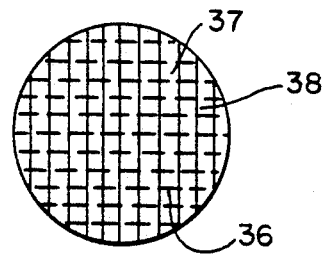
FIG. 5 is a schematic front elevational view of a lens incorporating a time varying shutter that is "nodalized" to provide one hundred nodes, each node under separate control in relation to the level of brightness sensed at a given node.

The discussion above has been directed primarily to the single "node" aspect of the invention as related to the spectacles or glasses shown in FIG. 1. With certain refinements of method and structure, many of the principles disclosed above may be applied to "nodalized" lenses, one of which is illustrated in FIG. 5. As there shown, the lens 36 comprises a lens including a liquid crystal that is responsive to the application of an electrical voltage in the same manner as previously discussed.

Figures 7, 8:
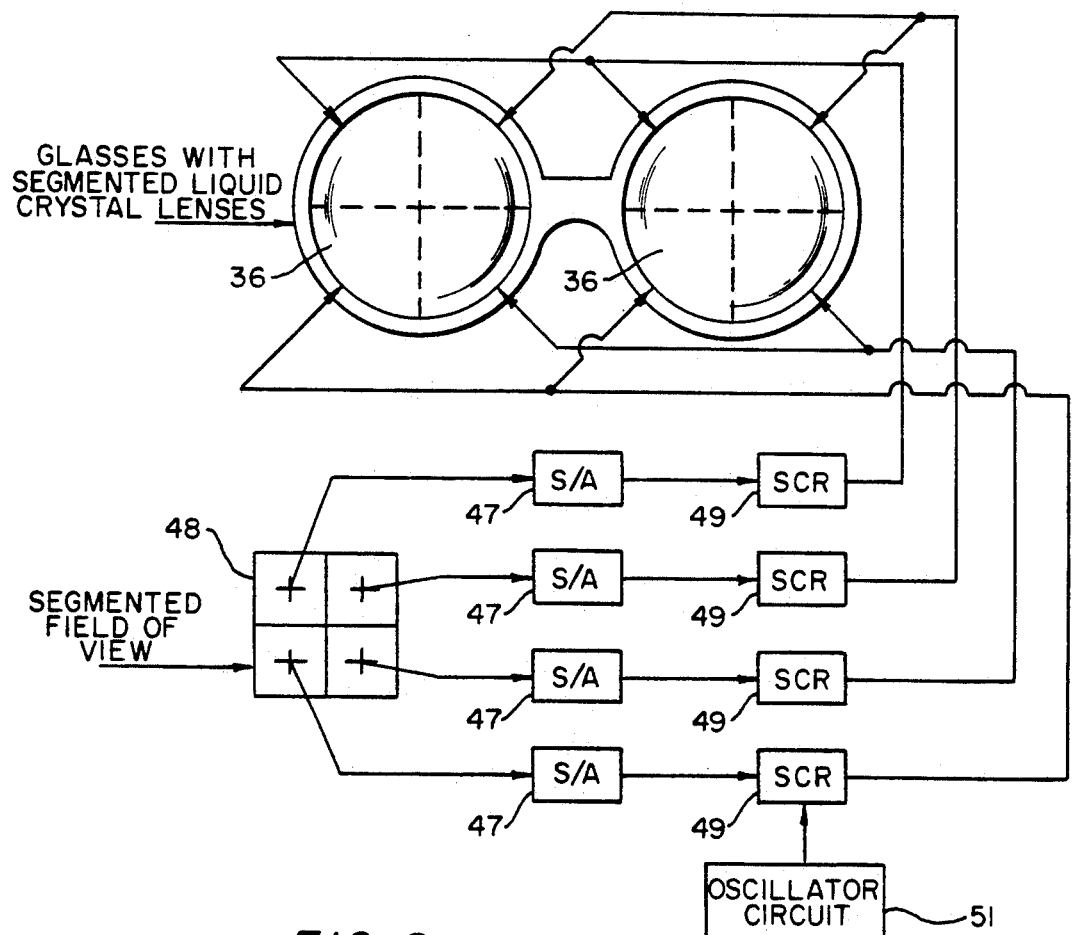
FIG. 7 is a composite graph that plots shutter position against time in connection with the three objects viewed in FIG. 6, with an indication of the coordinates of the specific node for each object viewed and the duty cycle of the control circuit in relation to each object viewed.
FIG. 8 is a simplified diagram of the operating circuitry for a multi-node time varying shutter as applied to the lenses of eye spectacles.

However, in the "nodalized" lens 36, which is shown duplicated in FIG. 8, the liquid crystal film is divided into a grid having as many separate "nodes" as may be necessary for a particular application. Thus, in FIG. 5, the lens 36 is shown divided into one hundred separate "nodes" 37 by the grid lines 38 which in the illustration indicate the boundaries between adjacent and independently responsive "nodes" that are not obvious to the naked eye, but each of which is controlled in the same manner as discussed above in connection with the single "node" concept comprising an entire lens area.

Whereas the lenses illustrated in FIGS. 1 and 4 may be categorized as time varying shutters (TVS), the lens of FIG. 5, and the lenses of the spectacles designated generally by the numeral 39 in FIG. 8 may be categorized as "nodalized time varying shutters" (NTVS) because each of the lenses contains a multiple number of nodes, with each node being independently controlled and acting like a single-node TVS system, and collectively dividing the field of view into multiple nodes that act in concert to affect the perceived brightness of objects visible in the field of view.

Figure 6:
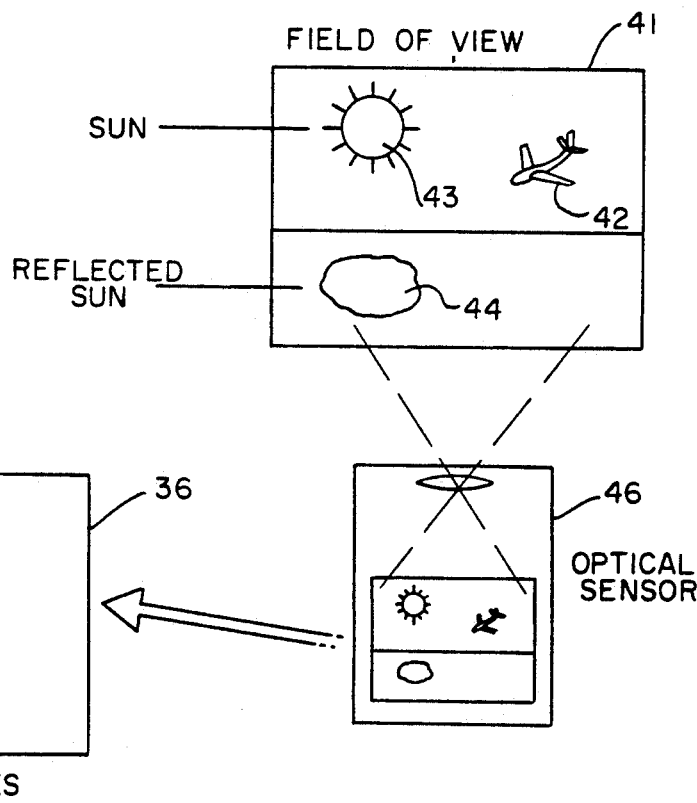
FIG. 6 is a schematic view illustrating the method of operation of a "nodalized" time varying shutter lens in relation to three objects viewed through the lens.

Thus, referring to FIG. 6, the utility of the multi-node lenses of FIGS. 5 and 8 is shown diagrammatically, where the field of view 41 included within the boundaries of the lenses includes an aircraft 42, the sun 43 and a lake 44. It may be assumed that the lenses are divided into a hundred nodes, but more or less nodes may of course be utilized. With a hundred nodes, each node represents 1% of the field of view. Optical sensors 46, of which there is one for each node, detect the light level at each node and use the light level to control the duty cycle of the control circuit for the lens as a whole and for each node in particular. In FIG. 6, node 3,3, for example, "sees" the sun as a very bright spot and initiates a 90% duty cycle in the control circuitry, i.e., the lens is closed 90% of the time and open only 10% of the time to thus drastically reduce the perceived brightness of the light rays from the sun.

Node 3,8 "sees" the reflected glare of the sun on the water of the lake and initiates a 50% duty cycle in the control circuitry, thus reducing the perceived glare by at least 50%, while the node 7,5 "sees" the open sky, including the aircraft, and initiates operation of the control circuitry at a duty cycle of only 10%, again altering the perceived brightness of the sky. These relationships are indicated visually and in tabular form in FIG. 7. The other ninety-seven nodes would operate similarly, each responding independently to the duty cycle imposed on the liquid crystal material to open or close the "shutter" represented by each node to thus modify the perceived brightness of the view visible through that particular "shutter".

The image perceived through a NTVS system is far superior to a single node TVS image under conditions where wide variations in light level exist in the field of view. In the example illustrated in FIG. 6, for instance, the NTVS system acts to selectively alter the perceived brightness (i.e., dim) the two excessively bright areas (the sun and its reflected glare) while leaving most of the remainder of the field of view (and particularly the aircraft) minimally affected. Because there is no color distortion with the NTVS system, the sky would still appear to be blue, but at a level of perceived brightness that is comfortable to the eye. It should be understood that it is not recommended that a wearer of sunglasses of any type look directly at the sun. However, it is believed that if such sunglasses embodied my NTVS structure, less damage to the eye would probably occur than if conventional sunglasses were used for this purpose. Comparing the operation of the NTVS system with the single node TVS system, it should be noted that with a TVS system, the degree of diminution of perceived brightness (dimming) would be based on the average brightness. The single node TVS image would be uniformly "dimmed", and although there would be no color distortion as occurs with conventional sunglasses, the image of the airplane in the example of FIG. 6 would not be as easily discernable as with the NTVS system.

The NTVS approach covers a wide range of system sophistication depending on the application. For example, an average person at the beach might find a NTVS system with as few as four nodes sufficient. Such a system would drastically reduce the perceived brightness of the sun, significantly "dim" the reflected glare from the water and reduce the brightness of the view visible through the other two quadrants by lesser amounts as required by the brightness of the light impinging on these quadrants and sensed by the optical sensors. For higher performance applications such as sports, more nodes would achieve improved capabilities of visual perception because the number of nodes determines the fineness with which brightness variations in the field of view can be controlled. This method of control of visual perception differs from the resolution control of a computer screen, for instance, where the number of pixles determines resolution, as limited by the resolution capabilities of the human eye.

The NTVS system can be extended to include utility in many of the methods conventionally used for computerized image enhancement. For example, in addition to reducing the perceived brightness of bright objects, e.g. direct sunlight, the NTVS system can also further reduce the perceived brightness of dark objects such as the sky to further improve the contrast between the sky and the aircraft in FIG. 6. More sophisticated systems could be used employing multiple optical sensors with filters to selectively reduce or enhance (by darkening the rest of the field) the perceived brightness of nodes based on color, polarization of light or other optical properties to enhance contrast. It is believed the novelty here lies in the nodalized method used to modify brightness within a realtime image, and not in the visual enhancement techniques which are widely used for still picture applications.

Thus, NTVS technology opens up the world of night vision to light level adjustment. The most immediate application involves night driving of an automobile. With the NTVS system embodied in glasses designed for night driving, the high intensity localized light sources such as the Halogen headlights of on-coming automobiles would be reduced in perceived brightness without affecting the brightness of the rest of the field of view. Such an application would enhance safety and reduce driver fatigue. It is a matter of personal experience for almost anyone that drives an automobile at night that some drivers do not change their high beam lights (bright) to their low beam lights (dim) when requested to do so by an on-coming driver. This would pose no problem to a driver wearing NTVS system driving glasses because the glasses would locally reduce the perceived brightness of the on-coming lights without affecting the higher ambient light level on the roadway. Other nighttime activities where NTVS system technology could be helpful include: night sports such as football and baseball where the glare of flood lights can interfere with a view of the ball, night flying, or even activities requiring frequent entry into and departure from brightly illuminated areas.

Other applications for NTVS system technology include the normally transparent panes of glass utilized in residential and commercial windows and in various transportation systems. Equipped with appropriate sensors, such windows could control for the occupants of a building the perceived brightness of light exteriorly of a building. Used as computer controlled "Venetian" blinds or shutters, windows equipped with the NTVS system could also function to prevent the interior of a residence or commercial building from being viewed from the outside, i.e., render the normally transparent window pane completely opaque, or control the passage of specific types of harmful rays that cause deterioration of the fabrics and other materials, such as plastics, from which many objects within a residence or commercial building are fabricated.

By selective control of specific multiple nodes on a pane of glass, for instance, various messages could be formed either by permitting the passage of light through a multiplicy of such nodes that spelled out the message, or by rendering such nodes opaque in a brighter background. In an automobile, for instance, a windshield constructed according to my invention could include the capability of displaying pertinent information on the windshield in front of the driver, such as "ADHERE TO SPEED LIMIT" or "TIRE PRESSURE LOW" or "REPLENISH GASOLINE". Many other such messages could of course be displayed, limited only by the imagination and the need for communication.

The operation of the multi-node NTVS system sunglasses may be more easily understood by referring to the block diagram illustrated in FIG. 8. This block diagram essentially replicates the block diagram illustrated in FIG. 4 and, as there, illustrates one very simple approach to implementing my NTVS system in a pair of spectacles or glasses. This illustration should in no way indicate that more elaborate circuits may not be used to control the duty cycle of the glasses, i.e., the fraction of time that light is blocked by the liquid crystal film during each oscillator circuit half cycle. Several sensor-/amplifier circuits 47 may be utilized, with each sensor-/amplifier circuit adapted to respond to the light intensity in one segment of the field of view 48. Each sensor-/amplifier outputs a different voltage based on the light intensity it senses. These voltages drive separate silicon controlled rectifier (SCR) circuits 49 driven by a common oscillator circuit 51, so that each SCR circuit produces a series of voltage pulses whose width relates to the light intensity in its dedicated segment of the field of view "seen" by the associated sensor/amplifier. These voltage pulses drive segmented liquid crystal films on the glasses so oriented that the segment on the glasses matches the segment of the field of view sampled by the correlated sensor. Each sensor/amplifier circuit and each SCR circuit operates independently to adjust the duty cycle on its segment of the glasses based on the average light intensity in the corresponding segment of the field of view. The sensor/amplifier circuits can have all the adjustment features noted above for the single node TVS system. In addition, they may communicate with each other to provide additional features. For example, rather than adjusting to create a uniform perceived brightness across the field of view, the sensor-/amplifier circuits can create an artificial degree of brightness contrast based on differences in light intensity in the field of view. For fine nodalization designs, this contrast could be based on the frequency content or on motion through the field of view. Such capability would aid visual descrimination of stationary objects of known color or of moving objects.

Having thus described the invention, what is believed to be patentable and sought to be protected by letters patent of the United States is as follows.

I claim:

1. As an article of manufacture, spectacles including at least one lens through which a field of view may b observed by a wearer of the spectacles, said lens comprising:
   a) a normally transparent body through which visual information passes to an observer when said spectacles are worn by the observer;
   b) at least two shutter means operatively incorporated in said lens and adjustable from said normally transparent high light transmissibility open state to a substantially non-transparent low light transmissibility closed state with each shutter means operable to control a different part of the observer's perceived field of view through the lens;
   c) an independent optical sensing device operatively associated with each shutter means for measuring the average intensity of light in the portion of the observer's field of view observable through the sensing device's shutter; and
   control means of cyclically independently opening and closing each shutter at a sufficiently high frequency that the observer perceives a continuous flickerless view of the portion of the field of view controlled by each shutter means with the level of brightness of the view perceived by the observer in each area of the field of view correlated to a shutter means being a function of the fraction of time during each cycle that each shutter means is in a high light transmissibility open state in response to selective control of the time interval that said shutter means is maintained in a substantially non-transparent low light transmissibility state.

2. The spectacles according to claim 1, wherein each said shutter means defines a "node" comprising a layer of liquid crystal material responsive to the application of an electrical charge thereto to oscillate light transmissibility thereof between said open and closed states.

3. The spectacles according to claim 2, wherein said control means comprises a light sensor/amplifier circuit operatively connected to each "node" and responsive to the intensity of light impinging thereon to output an electrical voltage proportional to the intensity of light impinging on the light sensor, a silicon controlled rectifier circuit connected to each said amplifier circuit to receive said electrical voltage, an oscillator circuit connected in common with all said silicon controlled rectifier circuits whereby each silicon controlled rectifier circuit outputs a series of voltage pulses having a width correlated to the light intensity in its dedicated segment of the field of view "seen" by the associated light sensor/amplifier circuit and correlated to the "node" to which the light sensor/amplifier circuit is connected.

4. The spectacles according to claim 3 further comprising a battery as a power source.

5. The spectacles according to claim 4, wherein the power source further comprises a solar cell.

6. The spectacles according to claim 4, wherein said spectacle include a frame on which said lenses are supported, a pair of temple members pivotally mounted on said frame for supporting the spectacles on the face of the wearer, and said control means is mounted on said spectacles and includes a control knob selectively adjustable by the wearer to set the desired level of brightness that suits the wearer's needs.

7. In conjunction with a liquid crystal spectacle lens presenting a visual field of view to a visual receptor where said spectacle lens is divided into at least two "nodalized" areas, the method of independently controlling the average brightness perceived by the visual receptor in each of the "nodalized" areas of the field of view, comprising the steps of:
   a) independently sensing the average intensity of light from the portion of the field of view that is perceived by the visual receptor through each "nodalized" area;
   b) causing the light transmissibility of each "nodalized" area to independently cycle between a state of high light transmissibility and a state of low light transmissibility at a frequency sufficiently high that the visual receptor perceived a continuous flickerless view through the portion of the field of view controlled by each "nodalized" area; and
   c) for each "nodalized" area, independently controlling the level of brightness perceived therethrough by controlling the fraction of time during each cycle that the "nodalized" area is in a state of high light transmissibility by controlling the portion of each cycle that the "nodalized" area is in a substantially non-transparent low light transmissibility state.

8. In conjunction with a liquid crystal spectacle lens presenting a visual field of view to a visual receptor where said spectacle lens is divided into a multiplicity of "nodalized" areas, the method of independently controlling the average brightness perceived by the visual receptor through each "nodalized" area of the spectacle lens, comprising the steps of:
   a) independently sensing the average intensity of light passing from the field of view that is observed by the visual receptor through each "nodalized" area;
   b) independently sensing the average time rate of increase of light intensity passing from the field of view that is observed by the visual receptor through each "nodalized" area;
   c) causing the light transmissibility of each "nodalized" area to cycle between a state of high light transmissibility and a state of low light transmissibility at a frequency sufficiently high that the visual receptor perceives a continuous flickerless view of the portion of the field of view controlled by each "nodalized" area; and
   d) for each "nodalized" area, independently controlling the time rate of increase of brightness perceived to be no greater than a brightness rate setpoint value by controlling the fraction of time during each cycle that the "nodalized" area is open to the transmission of light in response to selective control of the time interval that said shutter means is maintained in a substantially non-transparent low light transmissibility state.

9. In conjunction with a spectacle lens including a layer of electrically responsive normally transparent liquid crystal material presenting a visual field of view to a visual receptor where said layer of liquid crystal material on said spectacle lens is divided into a multiplicity of "nodalized" areas, the method of accumulating and applying energy for independently controlling the average brightness perceived by the visual receptor in each of the "nodalized" areas of the field of view, comprising the steps of:
 a) exposing a solar cell to sunlight for the generation of electrical energy;
 b) accumulating the electrical energy thus generated in an appropriate storage device;
 c) independently sensing the average intensity of light impinging on each "nodalized" area of the spectacle lens correlated to the field of view observed by the visual receptor through each "nodalized" area;
 d) applying electrical energy from the storage device to said liquid crystal material to cause the transmissibility of each "nodalized" area thereof to cycle between a state of normally transparent high light transmissibility and a state of substantially non-transparent low light transmissibility at a frequency sufficiently high that the visual receptor perceives a continuous flickerless view of the portion of the field of view controlled by each "nodalized" area; and
 e) for each "nodalized" area, independently controlling the brightness perceived to a predetermined maximum limit by controlling the fraction of time during each cycle that the "nodalized" area is open to the transmission of light in response to selective control of the time interval that said "nodalized" area is maintained in a substantially non-transparent low light transmissibility state.

10. In conjunction with a spectacle lens including a layer of electrically responsive liquid crystal material presenting a visual field of view to a visual receptor where said layer of liquid crystal material on said spectacle lens is divided into a multiplicity of "nodalized" areas, the method of independently controlling to a selected reference level brightness the average brightness perceived by the visual receptor in "nodalized" each area of the field of view, comprising the steps of:
 a) independently sensing the average intensity of light impinging on each "nodalized" area of the spectacle lens correlated to the field of view observed by the visual receptor through each "nodalized" area;
 b) adjusting a brightness set point to select the reference level brightness of light passing through each "nodalized" area of the spectacle lens;
 c) causing the transmissibility of each "nodalized" area of liquid crystal material to cycle between a state of high light transmissibility and a state of low light transmissibility at a frequency sufficiently high that the visual receptor perceives a continuous flickerless view through the portion of the field of view by each "nodalized" area; and
 d) for each "nodalized" area, independently controlling the brightness perceived to the set point selected reference level by controlling the fraction of time during each cycle that the "nodalized" area is open to the transmission of light.

11. As an article of manufacture, spectacles including a pair of lenses through each of which lenses a field of view may be observed by a wearer of the spectacles, each of said lenses comprising:
 a) a normally transparent body through which visual information passes to an observer when said spectacles are worn by the observer;
 b) at least two shutter means operatively incorporated in each of said lenses and adjustable from said normally transparent high light transmissibility open state to a substantially non-transparent low light transmissibility closed state with each shutter means of each lens operable to control a different part of the observer's perceived field of view through the lens;
 c) an independent optical sensing device operatively associated with each shutter means of each lens for measuring the average intensity of light in the portion of the observer's field of view observable through the sensing device's shutter; and
 d) control means for cyclically independently opening and closing each shutter at a sufficiently high frequency that the observer perceives a continuous flickerless view of the portion of the field of view controlled by each shutter means with the level of brightness of the view perceived by the observer in each area of the field of view correlated to a shutter means being a function of the fraction of time during each cycle that each shutter means is in a high light transmissibility open state in response to selective control of the fraction of time interval that said shutter means is maintained in a substantially non-transparent low light transmissibility state.

12. The spectacles of claim 11, wherein each said shutter means defines a "node" comprising a layer of liquid crystal material responsive to the application of an electrical charge thereto to oscillate light transmissibility thereof between said open and closed states.

13. The spectacles of claim 12, wherein said control means comprises a light sensor/amplifier circuit operatively connected to each "node" and responsive to the intensity of light impinging thereon to output an electrical voltage proportional to the intensity of light impinging on the light sensor, a silicon controlled rectifier circuit connected to each said amplifier circuit to receive said electrical voltage, an oscillator circuit connected in common with all said silicon controlled rectifier circuits whereby each silicon controlled rectifier circuit outputs a series of voltage pulses having a width correlated to the light intensity in its dedicated segment of the field of view "seen" by the associated light sensor/amplifier circuit and correlated to the "node" to which the light sensor/amplifier circuit is connected.

14. The spectacles of claim 13, further comprising a battery as a power source.

15. The spectacles of claim 14, wherein the power source further comprises a solar cell.

16. The spectacles of claim 13, wherein said spectacles include a frame on which said lenses are supported, a pair of temple members pivotally mounted on said frame for supporting the spectacles on the face of the wearer, and said control means is mounted on said spectacles and includes a control knob selectively adjustable by the wearer to set the desired level of brightness that suits the wearer's needs.

* * * * *